(12) United States Patent
Weeber et al.

(10) Patent No.: US 9,622,854 B2
(45) Date of Patent: Apr. 18, 2017

(54) APPARATUS, SYSTEM, AND METHOD FOR PROVIDING AN OPTICAL FILTER FOR AN IMPLANTABLE LENS

(71) Applicant: Abbott Medical Optics Inc., Santa Ana, CA (US)

(72) Inventors: Hendrik A. Weeber, Groningen (NL); Terrence B. Mazer, Albany, OH (US); Marrie H. Van Der Mooren, Engelbert (NL); Kaccie Y. Li, Groningen (NL); Huawei Zhao, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 8 days.

(21) Appl. No.: 14/195,568

(22) Filed: Mar. 3, 2014

(65) Prior Publication Data

US 2014/0324166 A1 Oct. 30, 2014

Related U.S. Application Data

(60) Provisional application No. 61/775,145, filed on Mar. 8, 2013.

(51) Int. Cl.
*A61F 2/16* (2006.01)
*G02C 7/10* (2006.01)

(52) U.S. Cl.
CPC .......... *A61F 2/1613* (2013.01); *A61F 2/1659* (2013.01); *A61F 2002/1696* (2015.04); *G02C 7/10* (2013.01)

(58) Field of Classification Search
USPC ...................... 623/6.18, 6.45, 6.13
See application file for complete search history.

(56) References Cited

U.S. PATENT DOCUMENTS

| | | | |
|---|---|---|---|
| 2008/0151183 A1* | 6/2008 | Altmann | G02C 7/04 351/159.6 |
| 2012/0008217 A1* | 1/2012 | Ishak et al. | 359/722 |
| 2012/0120365 A1* | 5/2012 | Legerton | G02B 27/0172 351/159.02 |

* cited by examiner

*Primary Examiner* — David H Willse
*Assistant Examiner* — Tiffany Shipmon
(74) *Attorney, Agent, or Firm* — Abbott Medical Optics Inc.

(57) ABSTRACT

An apparatus, system and method for providing an optical filter for an intraocular lens. The apparatus, system and method may include at least one optical filtering layer applied to at least one surface of the optic, wherein the optical filtering layer may at least partially filter light through the intraocular lens. The at least one optical filtering layer may include different types of optical filters including a neutral density filter, a chromatic filter, a photochromatic filter, and a polarizing filter. These filters may be used to reduce the transmission of light through the intraocular lens.

7 Claims, 10 Drawing Sheets

APPARATUS, SYSTEM, AND METHOD FOR PROVIDING AN OPTICAL FILTER FOR AN IMPLANTABLE LENS

CROSS-REFERENCES TO RELATED APPLICATIONS

This application claims priority to U.S. provisional application No. 61/775,145 filed on Mar. 8, 2013, the entire contents of which are incorporated herein by reference.

FIELD OF THE INVENTION

The instant disclosure relates to implantable lenses, and, more particularly, to an apparatus, system and method for providing an optical filter for an implantable lens.

BACKGROUND OF THE INVENTION

Surgery on the human eye has become commonplace in recent years. Many patients pursue eye surgery as an elective procedure, such as to avoid the use of contacts or glasses, and other patients may find it necessary to pursue surgery to correct an adverse condition in the eye. Such adverse conditions may include, for example, cataracts or presbyopia, as well as other conditions known to those skilled in the art that may negatively affect elements of the eye. For example, a cataract may increase the opacity of the lens of the eye, causing impaired vision or blindness. Correction of such adverse conditions may be achieved by surgically removing a diseased lens in the patient's eye and replacing it with an artificial lens, known as an intraocular lens (IOL).

The anatomy and physiology of the human eye is well understood. Generally speaking, the structure of the human eye includes an outer layer formed of two parts, namely the cornea and the sclera. The middle layer of the eye includes the iris, the choroid, and the ciliary body. The inner layer of the eye includes the retina. The eye also includes, physically associated with the middle layer, a crystalline lens that is contained within an elastic capsule, referred to herein as the lens capsule, or capsular bag.

Image formation in the eye occurs by entry of image-forming light to the eye through the cornea, and refraction by the cornea and the crystalline lens to focus the image-forming light on the retina. The retina provides the light sensitive tissue of the eye.

Functionally, the cornea has a greater, and generally constant, optical power in comparison to the crystalline lens. The power of the crystalline lens, while smaller than that of the cornea, may be changed when the eye needs to focus at different distances.

The iris operates to change the aperture size of the eye. More specifically, the diameter of the incoming light beam is controlled by the iris, which forms the aperture stop of the eye, and the ciliary muscles may contract, as referenced above, to provide accommodation in conjunction with any needed change in the size of the aperture provided by the iris. The opening, or aperture, in the iris is called the pupil.

Correction of defects or degradation in the aspects of the eye may occur surgically, as mentioned above, or non-surgically. In a simple example, it is common to wear glasses or contact lenses to improve vision by correcting myopic (near-sighted), hyperopic (far-sighted) and astigmatic eyesight. Rather than relying on glasses or contacts, elective laser refractive surgery, or other eye surgery, may serve to improve the refractive state of the eye, and may thereby decrease or eliminate dependence on glasses or contact lenses. Additional surgeries may include various methods of surgical remodeling of the cornea, or cataract surgery, for example. Surgery may also serve to implant an IOL, either in addition to the crystalline lens, which addition is referred to as a phakic IOL, or upon removal of the crystalline lens, which replacement is referred to as a pseudophakic IOL.

An IOL may be implanted in the eye, for example, as a replacement for the natural crystalline lens after cataract surgery, or to alter the optical properties of an eye in which the natural lens remains. As such, IOLs may be suitable for correcting vision disorders.

Owing to its thinner shape and the material from which it is made, the absorption of light in an IOL in much of the visible spectrum is negligible. Consequently, the IOL transmits a higher percentage of light than is transmitted by the natural crystalline lens. Thus, the perceived light intensity and/or the contrasting light intensity of objects viewed by an IOL patient may appear unusually bright. This extreme brightness may manifest itself to IOL patients in the form of an increased sensitivity to light. This increased sensitivity may simply annoy the IOL patient, or, of greater concern, may provide a deleterious effect to the IOL patient's ability to perform routine activities requiring acute vision.

A need therefore exists to reduce the light intensity induced by implanted IOLs in IOL patients.

SUMMARY OF THE INVENTION

An apparatus, system and method for providing an optical filter for an intraocular lens is disclosed. The apparatus, system and method may include at least one optical filtering layer applied to at least one surface of an optic, wherein the optical filtering layer may at least partially filter light through the intraocular lens. The at least one optical filtering layer may include one or more of various different types of optical filters, including a neutral density filter, a chromatic filter, a photochromatic filter, and a polarizing filter, by way of non-limiting example. These filters may be used to selectively or constantly reduce the transmission of light through the intraocular lens.

Thus, the present invention may limit or reduce the increased light intensity experienced by IOL implantation patients, and/or may negate the adverse side effects of implantation of a lens, such as an intraocular lens.

BRIEF DESCRIPTION OF THE FIGURES

Understanding of the present invention will be facilitated by consideration of the following detailed description of the preferred embodiments of the present invention taken in conjunction with the accompanying drawings, in which like numerals refer to like parts.

DETAILED DESCRIPTION OF THE PREFERRED EMBODIMENTS

It is to be understood that the figures and descriptions of the present invention have been simplified to illustrate elements that are relevant for a clear understanding of the present invention, while eliminating, for the purpose of clarity, many other elements found in typical lenses, lens systems and methods, and in optical filters and techniques. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

The present invention may reduce the intensity of light experienced by an implanted intraocular lens patient. In particular, optical filters may be used in the present invention to selectively or constantly attenuate areas of the visible spectrum, so as to reduce the brightness of light experienced by the implanted intraocular lens patient.

Figure 1:
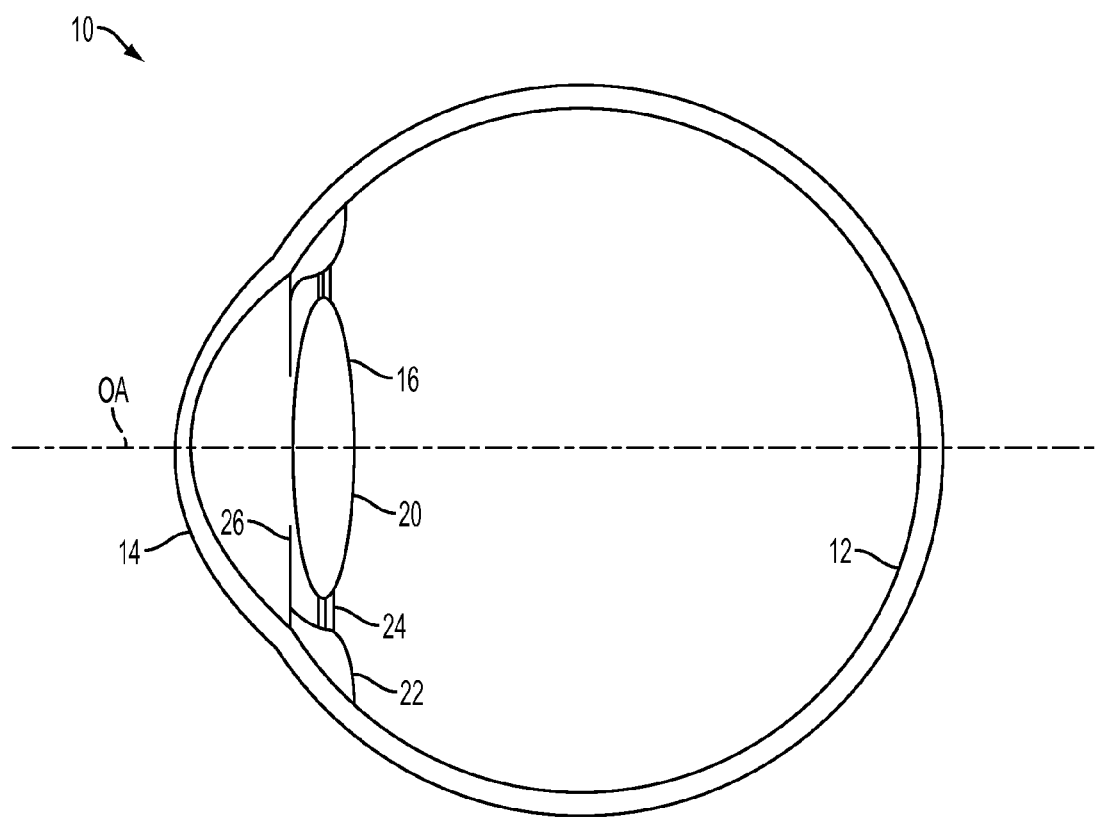
FIG. 1 illustrates a diagram of an eye.

FIG. 1 is a diagram of an eye. Eye 10 includes retina 12 for receiving an image produced by cornea 14 and natural lens 16 from light incident upon eye 10. Natural lens 16 is disposed within capsular bag 20, which separates anterior and posterior chambers of eye 10. Capsular bag 20 is a resilient material that changes the shape and/or location of natural lens 16 in response to ocular forces produced when ciliary muscles 22 contract and stretch natural lens 16 via zonules 24 disposed about an equatorial region of capsular bag 20.

Eye 10 also includes iris 26. Iris 26 may operate to change the aperture size of eye 10. More specifically, the diameter of the incoming light beam is controlled by iris 26, which forms the aperture stop of eye 10.

Figure 2:
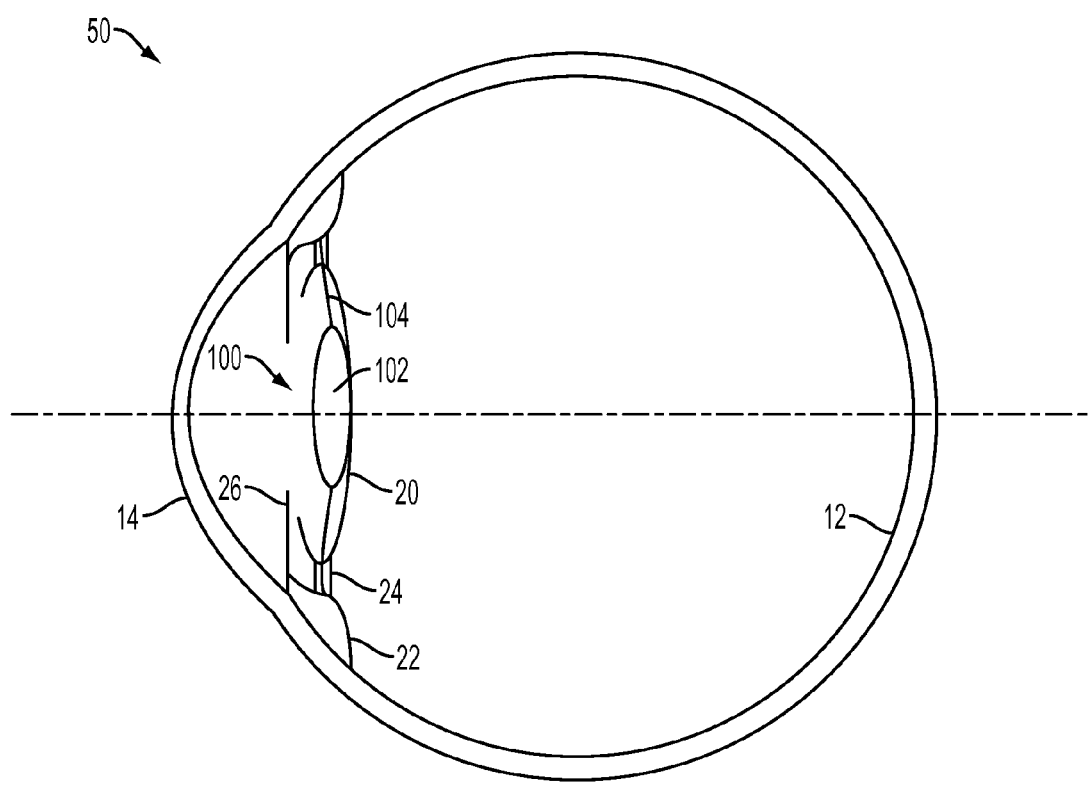
FIG. 2 illustrates a diagram of an eye with an implanted IOL.

Referring now to FIG. 2, there is shown an eye 10 having lens (natural lens 16 of FIG. 1) replaced with an IOL 100. Natural lens 16 may require removal due to a refractive lens exchange, or due to a disease such as cataracts, for example. Once removed, natural lens 16 may then be replaced by IOL 100 to provide improved vision in eye 10. Eye 10 may include IOL 100 with optic 102, cornea 14, retina 12, haptics or support structure 104 for centering optic 102.

The properties of the optic 102 materials typically permit more light to pass than the natural lens that is replaced. More particularly, in operation, when light passes through the lens of the eye (for example, natural lens 16 as shown in FIG. 1, or IOL 100 as shown in FIG. 2), some light is reflected at the surface of the lens, some is absorbed by the lens material, and some light is scattered. The percentage of the light passing completely through the lens for a given wavelength is the lens transmittance for that wavelength.

Figure 3:
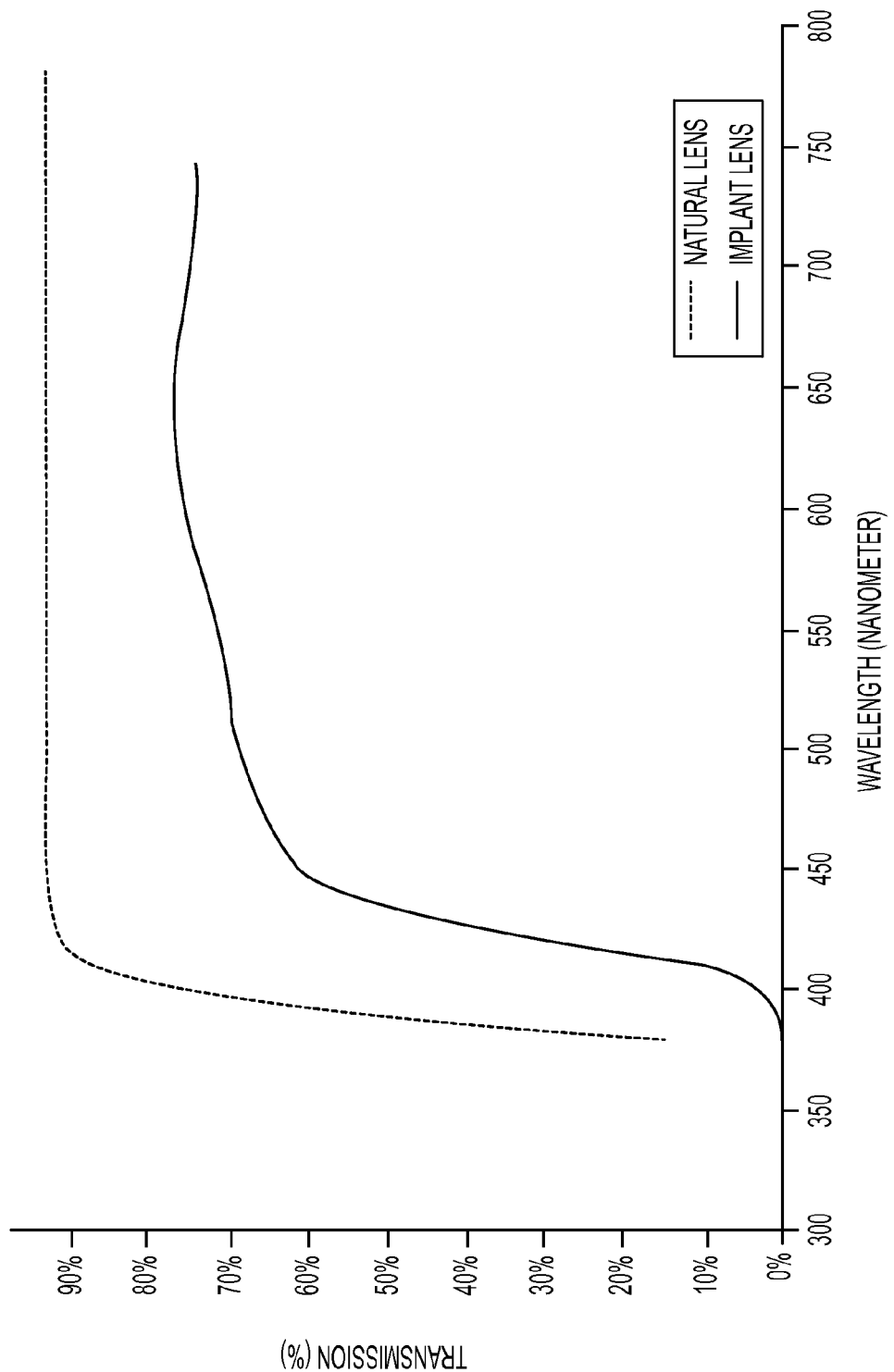
FIG. 3 illustrates a plot of transmittance versus wavelength of a typical natural crystalline lens and a typical implanted IOL.

FIG. 3 is a plot of transmittance versus wavelength of a typical natural crystalline lens (such as the lens 16 shown in FIG. 1), shown as the solid curve, and a typical IOL (such as the IOL 100 shown in FIG. 2), represented as the dashed curve. As evidenced from the curves, the typical IOL transmits a considerably higher percentage of light at nearly all wavelengths. This increased transmission of light can be very annoying to the patient, and may adversely affect the patient's ability to perform routine activities requiring acute vision.

Therefore, embodiments of the present invention provide an implantable intraocular lens containing optical filters that attenuate areas of the visible spectrum so as to reduce the intensity of light transmitted by the intraocular lens. This attenuation may be selective or constant, based on the filter design.

Figure 4:
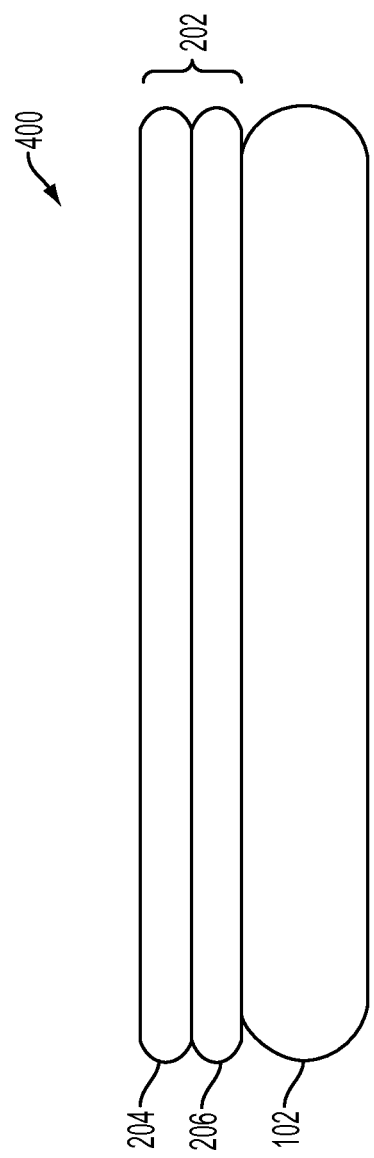
FIG. 4 illustrates an exemplary lens for use in the present invention.

Referring now to FIG. 4, there is shown a filter 202 formed on a lens of the type discussed herein, such as in the exemplary embodiments of FIG. 2, according to an aspect of the present invention. As illustrated, optical assembly 400 may include optic 102, such as the optics described hereinabove, and light attenuating filter 202. Filter 202, as shown in the exemplary embodiment of FIG. 4, may include at least one filter or filter layer. For example, a first filter layer 204 and second filter layer 206 may be provided on the anterior surface of optic 102. It should be noted that filter 202, and/or one of the one or more layers thereof, may also be applied to the posterior and/or to the posterior, and anterior, of the optic 102.

In an embodiment, optic 102 of IOL 100 contains filter 202 on the anterior surface thereof. Filter 202 may take the form of a neutral density filter, a chromatic filter, a photochromatic filter, a polarized filter, or the like.

Filter 202 may comprise gelatin, polymeric, or glass substrates, and may include impregnated or dissolved materials to reduce transparency. For example, organic dyes may be mixed with gelatin (in its liquid form) to achieve a desired optical density (OD). Filter 202 may include any number of stacked filters or filter layers, such as one, two, three, five, or more filters or filter layers to achieve desired performance characteristics and OD. Neutral density filters may be stacked together to achieve a desired density value, as the stacking of neutral density filters is an additive effect.

As is known to those skilled in the art, a neutral density filter is a light filter that decreases the intensity of light of all wavelengths or colors equally. Neutral density filters are characterized by the percent of incident light transmitted or by its OD.

Figure 5:
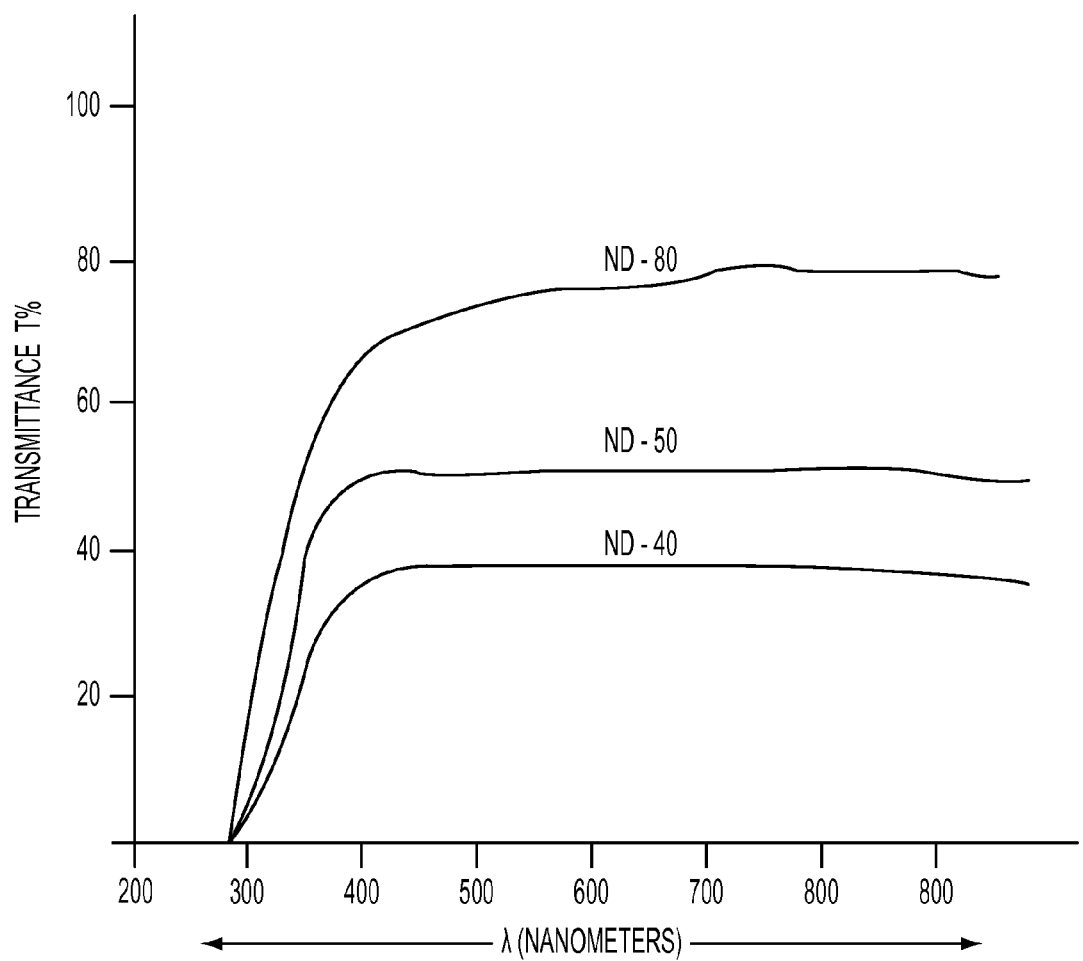
FIG. 5 illustrates a plot of light absorption profiles for various types of neutral density filters for use in the present invention.

FIG. 5 illustrates the additive effect of neutral density filters. There are shown light absorption profiles for a series of neutral density filters, ND-80, ND-50, and ND-40, having optical densities of 0.1, 0.3, and 0.4, respectively, and light transmission percentages of 80%, 50%, and 40%, respectively. As illustrated, applying a stack of a single ND-80 filter (density=0.1, transmission=80%) and a single ND-50 filter (density=0.3, transmission=50%) on an optic 102 is the equivalent of applying a single ND-40 filter, which has a density=0.4 and a transmission=40%.

In an alternative and additional embodiment to the use of a neutral density filter which filter 202 may relegate the light transmissivity characteristics to a designated portion of the electromagnetic spectrum (e.g., visual range, blue light region of visual range, etc.). A chromatic filter 202 may include one or more chromophores, otherwise known as photochromatic material. This photochromic material typically has spectral transmission characteristics. The photochromic material may cover the entire surface of the IOL 100, or may cover a particular portion, or region, of the surface. For example, a given region may block substantially all light of a first wavelength, and substantially no light at another wavelength. Photochromic compositions for use with embodiments of the present invention will at least partially reflect, or absorb, light in a portion of the visible spectrum. By way of non-limiting example, as certain wavelengths are known to be more disturbing to IOL patients (for example, those in the range of 570-650 nanometers), the chromatic filter employing particular photochromatic material(s) may be designed to absorb more light at these particular wavelengths.

According to further embodiments of the present invention, optic 102 of IOL 100 may comprise a polarizing filter 202. Polarizing filter 202 may take the form of a polarizing filter that blocks horizontally polarized light. The polarizing filter may comprise a polarized film material that is sandwiched between layers of a glass or plastic. More particularly, the polarized film material may comprise a thin sheet of polymer that has its molecules suitably aligned or oriented, such as by stretching in one direction. Subsequent treatment, such as with dyes and lamination, may form a single axis polarizer sheet that can then be applied as a filter layer to the IOL 100, as discussed above.

Figure 6:
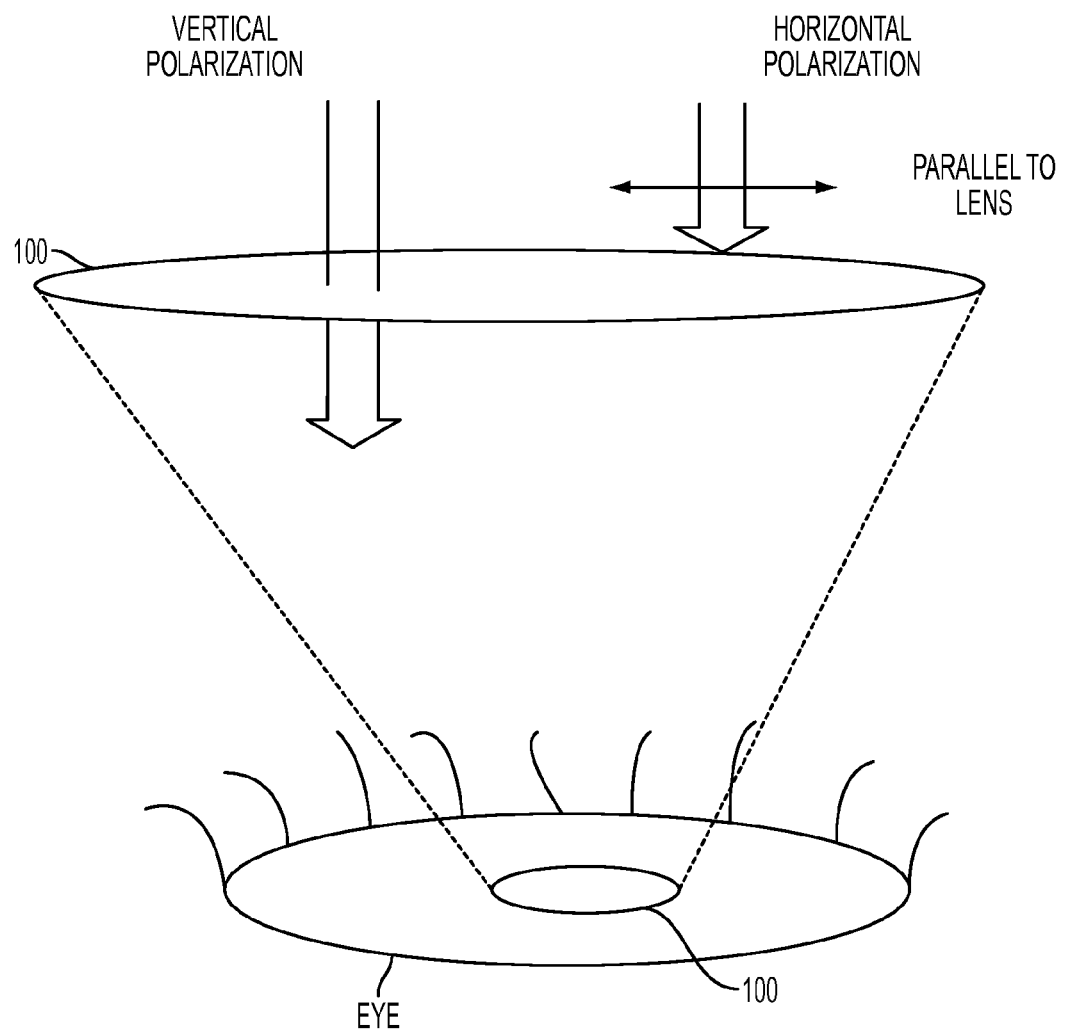
FIG. 6 illustrates shown a schematic top view of the function of an implanted IOL containing a vertically polarizing filter for use in the present invention.

Referring now to FIG. 6, there is shown a schematic top view of the function of a human eye implanted with an IOL 100, wherein the illustrated IOL includes a vertically polarized filter 202 associated with the optic 102 thereof. In the illustration, the filter 202 reflects a substantial portion of the horizontal polarized light (i.e., the light parallel to IOL 100), and transmits the bulk of the orthogonal vertical polarized light.

Figure 7:
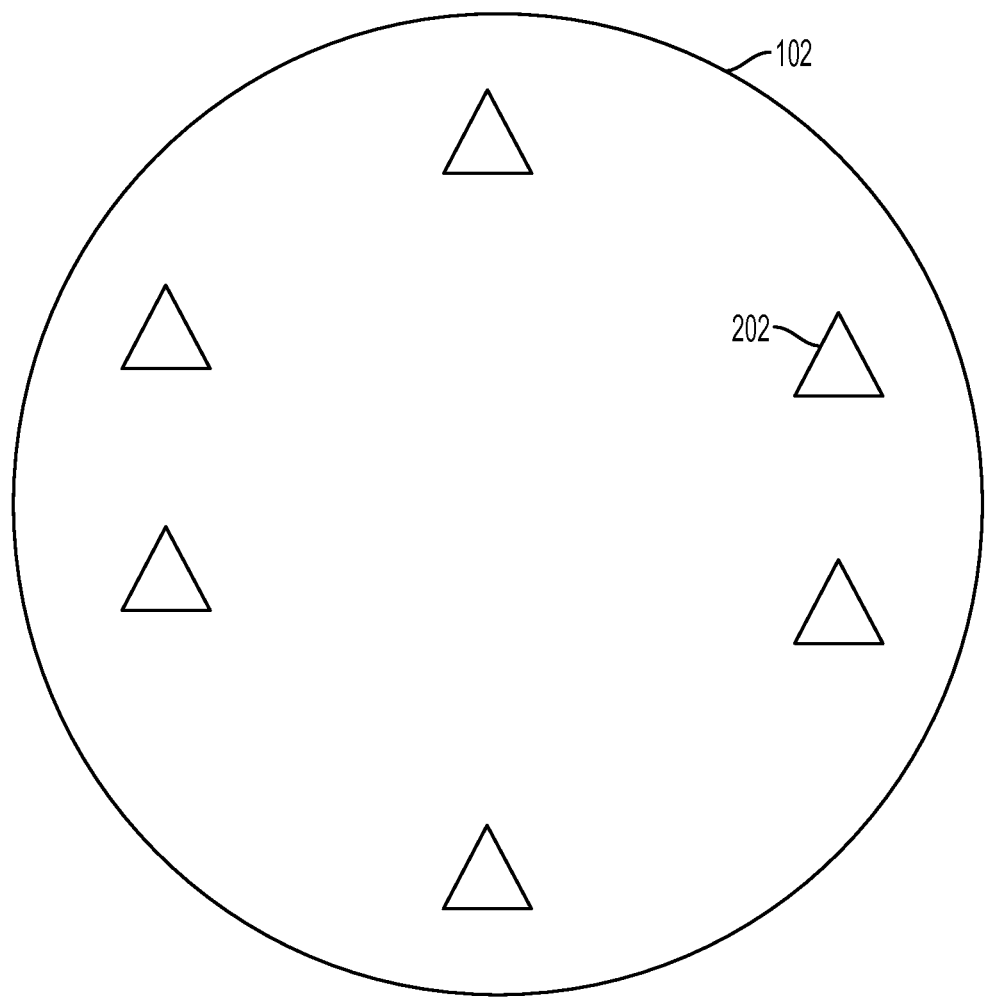
FIG. 7 illustrates an IOL containing optical filters in different zones for use in the present invention.

As an alternative to employing a vertically polarized filter, IOL 100 may include a circularly polarized filter, or may include a filter in which the upper and lower part of the lens block horizontal polarization, but the left and right sides block vertical polarization (or vice versa), by way of non-limiting example. Moreover, the IOL 100 may be divided into any number of zones of filters 202, wherein each zone may transmit a different polarization angle, as shown in FIG. 7. An eye 10 containing an IOL 100 having multiple zones having filters 202 transmitting different polarization angles will, of note always allow some transmission of light to reach the retina, even when light of a single polarization enters the eye (e.g. from a liquid crystal display screen), in accordance with the disclosed embodiments.

Embodiments of the present invention may include an intraocular lens having an optical filter 202 that changes filtering properties (for example, its absorption characteristics) depending upon levels of exposure to light. Those of skill in the art should appreciate that such filtering properties may be found in the aforediscussed photochromic material. For example, light sensitive photochromic molecules may be impregnated into an optical filter 202. When exposed to ultra-violet sunlight, a chemical reaction may quickly transform these molecules into colored light absorbers. Accordingly, for example, in the outdoors, ultra-violet rays may cause a chemical reaction, which may darken the IOL. Indoors, for example, in the absence of ultra-violet rays, the molecules return to their original form, and the intraocular lens may accordingly fade back to a clear state. The degree of darkening of the light sensitive molecules is directly proportional to the intensity of the light.

It should be noted that the optical properties of the optical filter 202 may change in other ways, in addition to the foregoing example, such as dependent upon the light level. For example, optical filter 202 may contain a material that changes polarization based on the light level. It should also be noted that the optical properties of the optical filter 202 may also change based on the spectral content of the incident light. For example, the intraocular lens may contain a material that changes polarization based on the wavelength of the incident light.

Embodiments of the present invention may include the use of multiple filters or multiple filter types, such as the use of two different types of polarizing filters to increase the dynamic range of light levels encountered by the eye without increasing the intensity of light incident on the retina.

Figure 8:
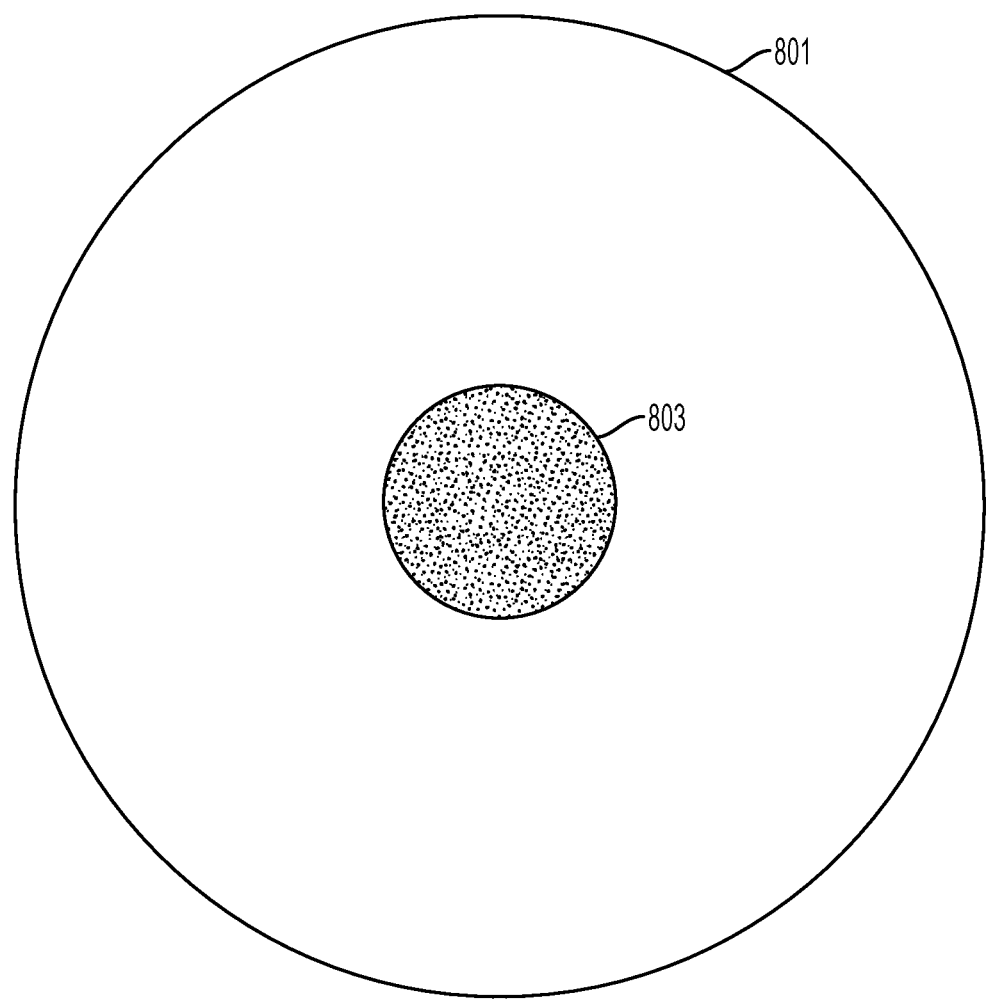
FIG. 8 illustrates a pupil containing a central obstruction according to an aspect of the present invention.

Referring now to FIG. 8, pupil 801 is shown with an obstruction in the center 803. This obstruction may be created by at least partially overlapping a horizontally polarized filter and a vertical filter. The polarizing filter of FIG. 8 comprises a polarized film material that is sandwiched between layers of a glass or plastic has its molecules aligned for the desired polarization, and includes with dyes or lamination.

Those skilled in the art will appreciate, in light of the disclosure, that various other elements may be employed with optic 102 and filter 202. For example, filter 202 may be provided in association with diffractive, refractive, extended depth of focus, pharmaceutical, or other elements to obtain desired optical or treatment characteristics.

Figure 9:
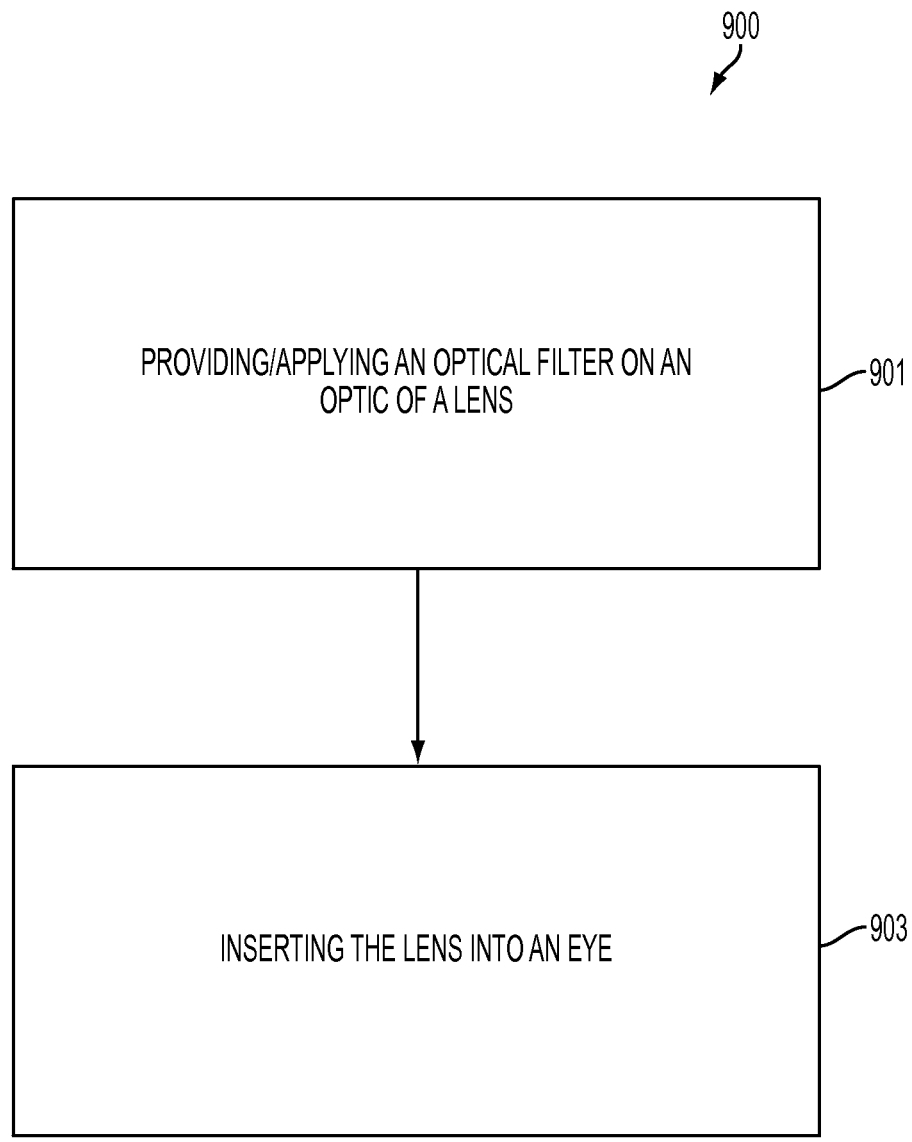
FIG. 9 illustrates a method of providing an optical filter on a lens according to an aspect of the present invention.

FIG. 9 illustrates a method 900 for reducing the transmission of light through an intraocular lens. Method 900 may include providing/applying a lens having an optical filter at step 901. This optical filter may include any optical filter as discussed hereinthroughout. Included within this optical filter layer, such as underlying or overlaying same, may be an impregnating substance, as discussed hereinthroughout, and included may be other optical or chemical elements in conjunction with the optical filter layer. Method 900 may further include providing the lens in a manner suitable for insertion of the lens into an eye at step 902. This insertion may include folding/unfolding, injecting, and the like, as described herein.

According to other embodiments of the present invention, optic 102 of IOL 100 may comprise an optical filter 202 that takes the form of a light diffusing filter that scatters light in a uniform manner. More specifically, this light diffusing filter may induce an extremely uniform scatter within the eye. This uniform scatter may be produced by particles slightly smaller than the wavelength of light, and may thereby create a uniform background comprising soft light. For example, these particles may be of a wavelength slightly less than 380 nm. Due to this uniformity, the eye will discard the background so that any contrast sensitivity will not be affected. The light diffusing filter may take the form of a film which includes a flexible polymer substrate (e.g., polycarbonate, etc.) coupled to an optical diffuser material (e.g., UV-curable epoxy) with a plurality of features (e.g., embossed using a pressed or rolled master pattern via lathe cutting) for diffusing light.

Embodiments of the present invention may also include an optical filter 202 that may take the form of a minus filter. A minus filter may include multilayer film structures comprising alternate layers of a high refractive index and a low refractive index. In particular, such a minus filter may be realized by forming the at least one high refractive index layer having a greater thickness than the at least one low refractive index layer.

As used herein, "high refractive index" refers to a refractive index of about 2.00 to 2.50, and "low refractive index" refers to a refractive index of about 1.37 to 1.52. As an example, the composite layer may be comprised of a stack of alternative layers composed of titanium dioxide ($TiO_2$) and silicon dioxide ($SiO_2$). The thickness of the individual layers may generally be about 5 nm to about 30 nm, and the individual layers of the composite layer may be deposited by a PEG machine, for example.

The different layers may be further selected such that reflection of visible light at an interface of the filter with air is sufficiently low so as to minimize glare. Glare at a concave (rear) IOL surface may result from reflection of incident light at the concave surface. For a lens with no IOL and/or filter included, a portion of incident light at the eye surface would be reflected from the concave surface of the lens towards the eye, and additionally, a portion of the non-reflected light passing through the substrate would be reflected from the convex surface of the lens substrate towards the eye.

According to embodiments of the present invention, reflectance at the concave IOL surface may be reduced because the filter 202 thereon may be designed to provide antireflection. Additionally, one of the layers (e.g., an absorbing layer) may serve to further reduce reflected light. Any non-reflected light at this surface must pass through the absorbing layer twice, once upon entering the filter, and again after passing through the substrate and being reflected from the convex surface. Therefore, those of skill in the art will appreciate that each pass through the absorbing layer reduces the transmittance of light therethrough.

Figure 10:
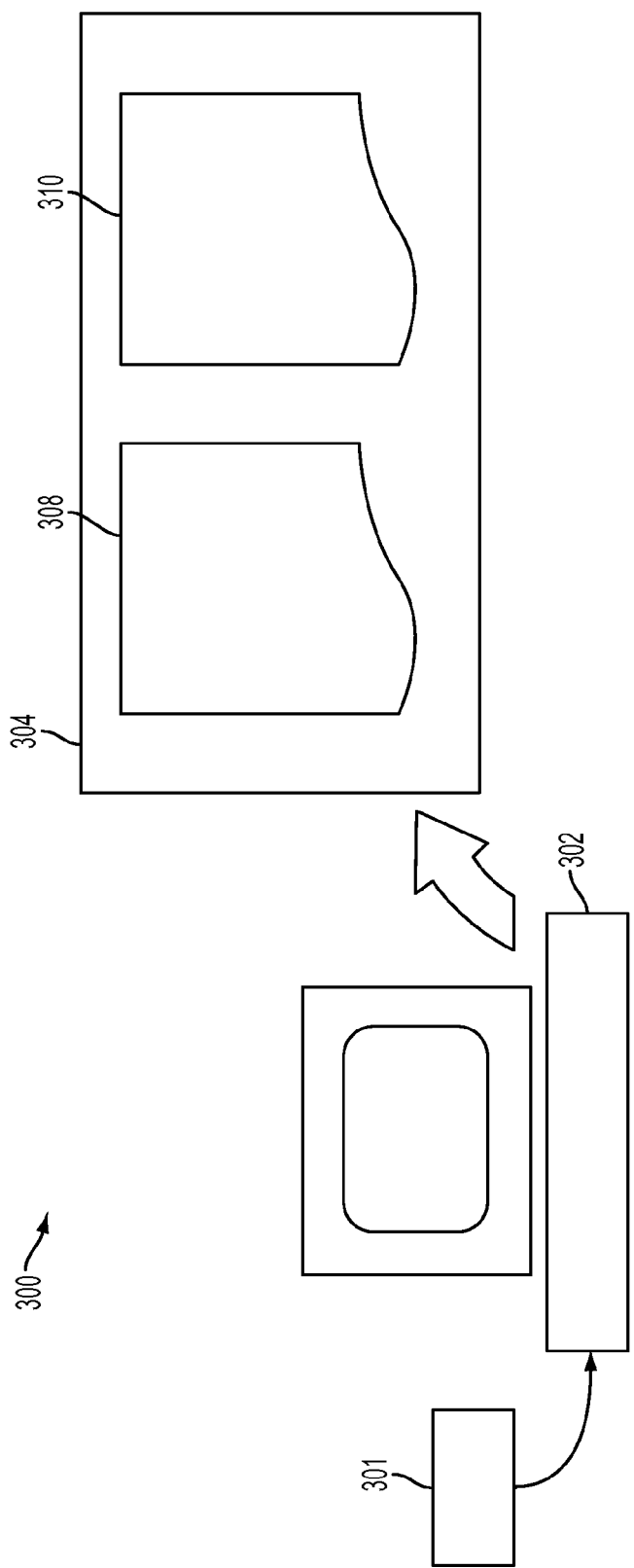
FIG. 10 is a graphical representation of the elements of computing system for selecting an intraocular lens.

FIG. 10 is a block diagram illustrating the implementation of the present invention in a clinical system 300 comprised of one or more apparatuses that are capable of assessing the eye's biometry and of performing the calculations and comparisons set forth in method 900. The system 300 may include a biometric reader and/or biometric simulation input 301, a processor 302, and a computer readable memory 304 coupled to the processor 302. The computer readable memory 304 includes therein an array of ordered values 308 and sequences of instructions 310 which, when executed by the processor 302, cause the processor 302 to select an implantable IOL configured for implantation into the eye of the subject presenting the biometric readings to biometric reader 301. The array of ordered values 308 may comprise data used or obtained from method 900 or other methods consistent with embodiments of the invention. For example, the array of ordered values 308 may comprise one or more desired light transmission and/or refractive outcomes, parameters of an eye model based on one or more characteristics of at least one eye, and data related to characteristics of an IOL or set of IOLs, such as a transmissivity, an optical power, an aspheric profile, and/or a lens plane.

The sequence of instructions 310 may include one or more steps of method 900 or other methods consistent with embodiments of the invention. In some embodiments, the sequence of instructions 310 includes designing a filter having desired light transmittance characteristics.

The processor 302 may be embodied in a general purpose desktop or laptop computer, and/or may comprise hardware associated with biometric reader 301 specifically for selecting an IOL for placement into the eye of the subject. In certain embodiments, the system 300 may be configured to be electronically coupled to another device, such as one or more instruments for obtaining measurements of an eye or a plurality of eyes in conjunction with, or in addition to, biometric reader 301. Alternatively, the system 300 may be embodied in a handheld device that may be adapted to be electronically and/or wirelessly coupled to one or more other devices.

Although the invention has been described and pictured in an exemplary form with a certain degree of particularity, it is understood that the present disclosure of the exemplary form has been made by way of example, and that numerous changes in the details of construction and combination and arrangement of parts and steps may be made without departing from the spirit and scope of the invention as set forth in the claims hereinafter.

The invention claimed is:

1. An intraocular lens including an optical filter to reduce the transmission of light through the intraocular lens, comprising:
    at least one optic disposed about an optical axis, wherein the at least one optic comprises an anterior surface and an opposing posterior surface, the surfaces configured to transmit light through the intraocular lens to a retina of an eye when implanted within a capsular bag of the eye; and
    a single optical filtering layer formed on an exterior of at least one of the surfaces of the optic, for the purpose of at least partially reducing light transmission through the intraocular lens; wherein the single optical filtering layer comprises a horizontally polarized filter at least partially overlapping a vertical polarizing filter.

2. The intraocular lens of claim 1, further comprising at least one additional optical filtering layer applied to an exterior of at least one of the surfaces of the optic.

3. The intraocular lens of claim 1, wherein the single optical filtering layer comprises a plurality of optical filtering layers with at least one neutral density filter.

4. The intraocular lens of claim 1, wherein the single optical filtering layer comprises a plurality of optical filtering layers with at least one a chromatic filter.

5. The intraocular lens of claim 1, wherein the single optical filtering layer comprises a plurality of optical filtering layers with at least one photochromatic filter.

6. The intraocular lens of claim 1, wherein the single optical filtering layer comprises a plurality of optical filtering layers with at least one additional polarizing filter.

7. The intraocular lens of claim 6, wherein the polarizing filter is a circularly polarizing filter.

* * * * *